(12) United States Patent
Boutillette et al.

(10) Patent No.: US 10,549,069 B2
(45) Date of Patent: *Feb. 4, 2020

(54) CATHETER WITH FORMED GUIDE WIRE RAMP

(71) Applicant: BOSTON SCIENTIFIC SCIMED, INC., Maple Grove, MN (US)

(72) Inventors: Michael P. Boutillette, Waltham, MA (US); James E. Windheuser, Hopkinton, MA (US); Oscar R. Carrillo, Jr., Attleboro, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 163 days.

This patent is subject to a terminal disclaimer.

(21) Appl. No.: 15/807,559

(22) Filed: Nov. 8, 2017

(65) Prior Publication Data

US 2018/0064911 A1 Mar. 8, 2018

Related U.S. Application Data

(60) Continuation of application No. 14/334,359, filed on Jul. 17, 2014, now Pat. No. 9,814,861, which is a
(Continued)

(51) Int. Cl.
*A61M 25/01* (2006.01)
*A61M 25/00* (2006.01)
(Continued)

(52) U.S. Cl.
CPC .... *A61M 25/0172* (2013.01); *A61M 25/0029* (2013.01); *A61M 25/0108* (2013.01);
(Continued)

(58) Field of Classification Search
CPC .......... A61M 25/0169; A61M 25/0172; A61M 2025/0177; A61M 2025/018;
(Continued)

(56) References Cited

U.S. PATENT DOCUMENTS 4,552,554 A * 11/1985 Gould .................. A61M 25/01
604/104
5,135,535 A 8/1992 Kramer
(Continued)

FOREIGN PATENT DOCUMENTS

JP 6507811 A 9/1994
WO 9220397 A1 11/1992
(Continued)

OTHER PUBLICATIONS

International Search Report for International Application No. PCT/DE2009/000805.
(Continued)

*Primary Examiner* — Andrew M Gilbert
(74) *Attorney, Agent, or Firm* — Seager, Tufte & Wickhem, LLP

(57) ABSTRACT

A rapid exchange catheter comprises a guide wire lumen including a substantially sealed portion in which a lumen wall extends around an entire periphery thereof and a channel portion including a channel opening the lumen to an exterior of the catheter, wherein a width of the channel is less than a maximum width of the channel portion. A guide wire ramp extends into the channel portion, with the ramp extending further into the lumen of the channel portion as a distal end of the ramp is approached.

20 Claims, 3 Drawing Sheets

Related U.S. Application Data continuation of application No. 13/782,281, filed on Mar. 1, 2013, now Pat. No. 8,784,362, which is a continuation of application No. 12/437,281, filed on May 7, 2009, now Pat. No. 8,388,876, which is a division of application No. 10/268,135, filed on Oct. 8, 2002, now Pat. No. 7,534,223.

(51) Int. Cl.
  *B26D 7/00* (2006.01)
  *A61M 25/10* (2013.01)
(52) U.S. Cl.
  CPC ......... *B26D 7/00* (2013.01); *A61M 2025/004* (2013.01); *A61M 2025/0008* (2013.01); *A61M 2025/0177* (2013.01); *A61M 2025/0183* (2013.01); *A61M 2025/0188* (2013.01); *A61M 2025/107* (2013.01); *Y10T 83/0405* (2015.04)
(58) Field of Classification Search
  CPC ...... A61M 2025/0183; A61M 25/0029; A61M 25/0015
  See application file for complete search history.

(56) References Cited

U.S. PATENT DOCUMENTS

| | | | |
|---|---|---|---|
| 5,263,932 A | 11/1993 | Jang | |
| 5,320,602 A | 6/1994 | Karpiel | |
| 5,324,269 A | 6/1994 | Miraki | |
| 5,334,986 A | 8/1994 | Fernhout | |
| 5,360,416 A * | 11/1994 | Ausherman | A61B 17/3401 604/158 |
| 5,364,376 A * | 11/1994 | Horzewski | A61M 25/0169 604/247 |
| 5,389,087 A * | 2/1995 | Miraki | A61M 25/104 604/160 |
| 5,394,333 A | 2/1995 | Kao | |
| 5,395,335 A | 3/1995 | Jang | |
| 5,397,302 A | 3/1995 | Weaver et al. | |
| 5,416,712 A | 5/1995 | Geier et al. | |
| 5,458,613 A | 10/1995 | Gharibadeh et al. | |
| 5,462,530 A | 10/1995 | Jang | |
| 5,540,236 A | 7/1996 | Ginn | |
| 5,554,118 A | 9/1996 | Jang | |
| 5,563,786 A | 10/1996 | Torii | |
| 5,919,164 A | 7/1999 | Andersen | |
| 5,921,971 A | 7/1999 | Agro et al. | |
| 6,007,522 A * | 12/1999 | Agro | A61M 25/0097 604/264 |
| 6,152,910 A * | 11/2000 | Agro | A61M 25/0028 604/264 |
| 6,249,246 B1 | 6/2001 | Bode et al. | |
| 6,278,945 B1 | 8/2001 | Lin | |
| 6,401,036 B1 | 6/2002 | Geier et al. | |
| 6,408,245 B1 | 6/2002 | An et al. | |
| 6,475,187 B1 * | 11/2002 | Gerberding | A61M 25/0054 600/435 |
| 6,502,033 B1 | 12/2002 | Phuyal | |
| 6,577,952 B2 | 6/2003 | Geier et al. | |
| 6,592,549 B2 * | 7/2003 | Gerdts | A61F 2/95 604/103.04 |
| 6,597,987 B1 | 7/2003 | Barton | |
| 6,702,781 B1 | 3/2004 | Reifart et al. | |
| 6,931,322 B2 | 8/2005 | Jung et al. | |
| 7,115,109 B2 | 10/2006 | Gerdts et al. | |
| 7,274,504 B2 | 9/2007 | Crane et al. | |
| 7,534,223 B2 | 5/2009 | Boutilette et al. | |
| 7,603,233 B2 | 10/2009 | Tashiro | |
| 7,987,047 B2 | 7/2011 | Ishigami et al. | |
| 8,388,876 B2 | 3/2013 | Boutilette et al. | |
| 8,784,362 B2 | 7/2014 | Boutilette et al. | |
| 9,814,861 B2 * | 11/2017 | Boutillette | A61M 25/0029 |
| 2002/0133118 A1 | 9/2002 | Gerdts et al. | |
| 2002/0143251 A1 * | 10/2002 | Richardson | A61M 25/0023 600/434 |
| 2002/0177841 A1 * | 11/2002 | Moloney | A61M 25/0052 604/528 |
| 2003/0036847 A1 | 2/2003 | Geier et al. | |
| 2003/0040769 A1 | 2/2003 | Kelley et al. | |
| 2003/0045836 A1 * | 3/2003 | Batiste | A61M 25/01 604/164.13 |
| 2003/0153934 A1 | 8/2003 | Gerberding | |
| 2005/0171473 A1 | 8/2005 | Gerdts et al. | |
| 2008/0091347 A1 | 4/2008 | Tashiro | |
| 2011/0071755 A1 | 3/2011 | Ishigami et al. | |

FOREIGN PATENT DOCUMENTS

| | | |
|---|---|---|
| WO | 9222345 A1 | 12/1992 |
| WO | 0050917 A1 | 8/2000 |
| WO | 0069499 A1 | 11/2000 |
| WO | 0158383 A2 | 8/2001 |
| WO | 02074378 A1 | 1/2002 |
| WO | 2005076031 A2 | 8/2005 |

OTHER PUBLICATIONS

Written Opinion for International Application No. PCT/DE2009/000805 (undated).

* cited by examiner

CATHETER WITH FORMED GUIDE WIRE RAMP

RELATED APPLICATIONS

The present application is a continuation of U.S. patent application Ser. No. 14/334,359, filed Jul. 17, 2014, now U.S. Pat. No. 9,814,861, which is a continuation of U.S. patent application Ser. No. 13/782,281, filed Mar. 1, 2013, now U.S. Pat. No. 8,784,362 which is a continuation of U.S. patent application Ser. No. 12/437,281 filed May 7, 2009, now U.S. Pat. No. 8,388,876, which is a divisional of U.S. patent application Ser. No. 10/268,135 filed Oct. 8, 2002, now U.S. Pat. No. 7,534,223, the entire disclosures of which are incorporated herein by reference.

BACKGROUND INFORMATION

Endoscopic procedures for treating abnormal pathologies within the alimentary canal system and biliary tree (including the biliary, hepatic and pancreatic ducts) are increasing in number. The endoscope provides access to the general area of a desired duct using direct visualization. However, the duct itself must be navigated using a catheter in conjunction with fluoroscopy and guide wires.

If visualization of the common bile duct is desired, the guide wire is guided into the common bile duct and the catheter is advanced over the guide wire until the distal end thereof is positioned at a desired location for delivery of the contrast media for fluoroscopic visualization of the anatomical detail within the common bile duct.

Visualization may reveal selected areas within the common bile duct that require treatment. To treat the selected areas, a different catheter is typically required, necessitating a catheter exchange. A catheter exchange typically involves removing the first catheter from the endoscope, over the guide wire, and advancing a second catheter over the guide wire to the desired treatment site. Once the guide wire is in place relative to the targeted area, it is highly desirable to maintain the position of the guide wire during subsequent catheter procedures, including during a catheter exchange procedure. If the guide wire moves during such a procedure, the guide wire may need to be re-directed through the body ducts to the target site, which is often a difficult and time consuming task.

In addition to performing a catheter exchange procedure, it may be desirable at times to perform a guide wire exchange procedure, for example, when a first guide wire is too large to fit through a desired body duct, or otherwise lacks the characteristics desired for a particular application. Under these circumstances, a physician may leave the catheter in place and withdraw the first guide wire from the catheter. The physician then inserts a second guide wire through the catheter to the desired site. Thus, once the catheter has been properly positioned at a target site, it is highly desirable to maintain the position of the catheter during a guide wire exchange procedure so that the second guide wire may be guided directly to the desired site.

To maintain the position of the guide wire and/or catheter, a physician typically must grasp the proximal end of the guide wire and/or catheter with one hand and perform the corresponding exchange with the other. This is difficult, and often results in the movement of the guide wire and/or catheter. Alternatively, additional devices such as guide wire extenders may be used. However, utilizing such additional devices adds to the complexity of and the time required for the exchange.

SUMMARY OF THE INVENTION

The present invention is directed to a rapid exchange catheter comprises a guide wire lumen including a substantially sealed portion in which a lumen wall extends around an entire periphery thereof and a channel portion including a channel opening the lumen to an exterior of the catheter, wherein a width of the channel is less than a maximum width of the channel portion. A guide wire ramp extends into the channel portion, with the ramp extending further into the lumen of the channel portion as a distal end of the ramp is approached.

DETAILED DESCRIPTION

Figure 1:
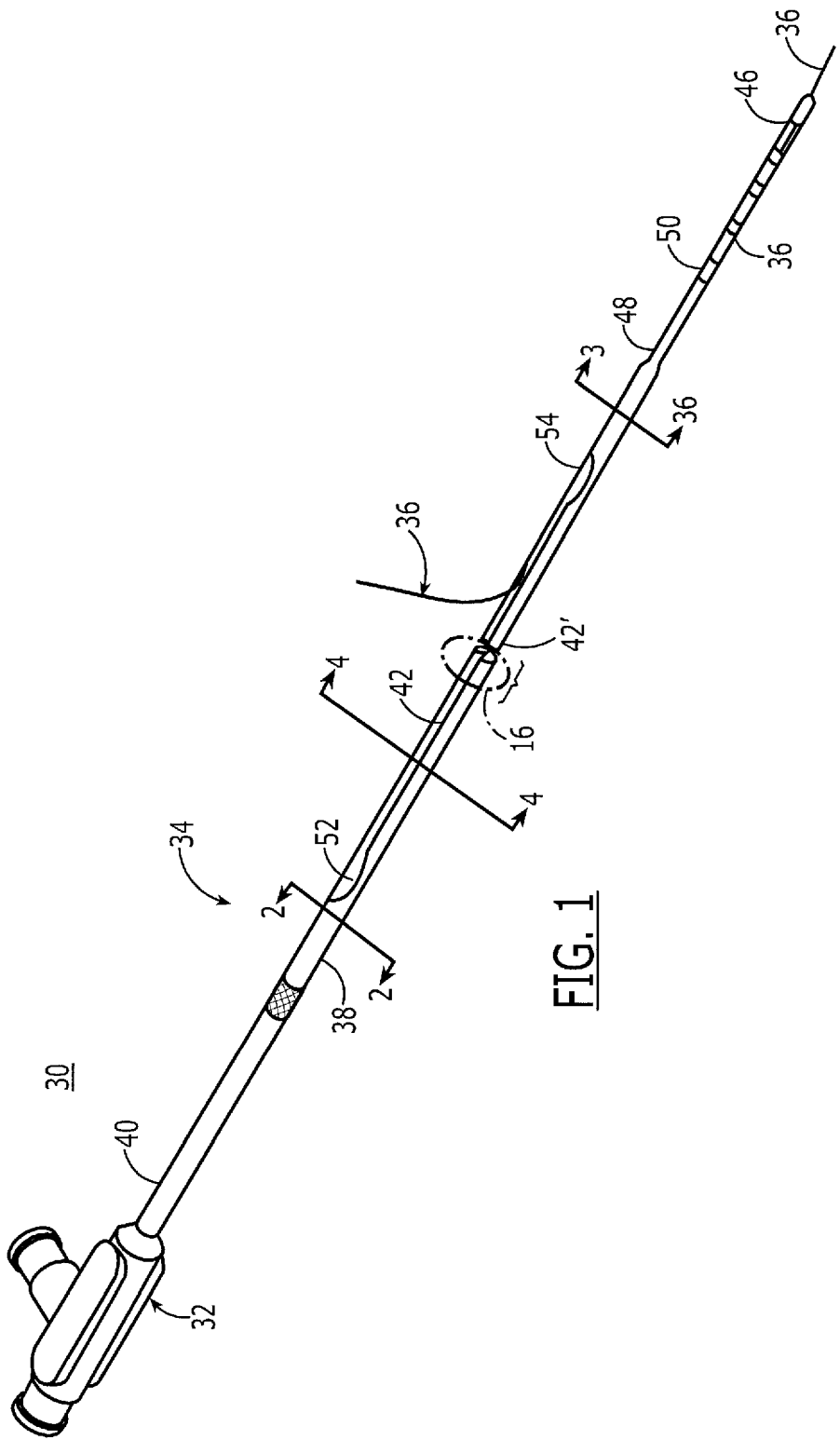
FIG. 1 shows an exemplary embodiment of a catheter according to the present invention in a perspective view having a C-shaped channel and guide wire lumen for directing a guide wire along its shaft and for facilitating rapid catheter exchange.

FIGS. 1-6 show an exemplary embodiment of a catheter assembly 30 according to the present invention. The catheter assembly 30 is used in catheter procedures for accessing targeted anatomical regions through the alimentary canal. The present invention incorporates features that allow rapid exchange of a catheter by a single operator. The catheter of the present invention allows shorter length guide wires to be used, resulting in procedures which require less medical personnel, are less time consuming, and less costly. Additionally, the present invention is adaptable to a variety of catheter devices used for catheter procedures within the alimentary canal or any other body lumen.

The catheter assembly 30 includes a catheter hub assembly 32 and a catheter 34, having a guide wire 36 passing through a guidewire lumen 60, (shown in FIGS. 2 and 3) extending therethrough. The catheter 34 includes a shaft 38 which has a proximal end 40, a C-channel 42, a distal tip region 44, a distal end 46 and various lumens described in greater detail below. The catheter hub assembly 32 is operably connected to a proximal end 40 of the shaft 38. The catheter hub assembly 32 is preferably configured to couple to ancillary devices allowing access to a lumen within the shaft 38.

The shaft 38 may preferably be a generally tubular member having a generally uniform outer shape at the proximal end 40. As would be understood by those of skill in the art, the shaft 38 may be sized for slidable passage through the lumen of an endoscope (not shown) or through a body lumen. The shaft 38 is preferably formed in an extrusion process, and may be formed of a polymeric material. In one embodiment, the preferred polymeric material is polytetrafluoroethylene, polyether block amide, nylon or a combination or blend of these. Catheters that are contemplated include, but are not limited to, cannulas, sphincterotomes, cytology devices, and devices for stone retrieval and stent placement.

In a preferred embodiment, the shaft 38 may further include a distal taper 48 that tapers to the distal tip region 44. Additionally, the distal tip region 44 may, for example, include high contrast, color-coded distal markers 50. Finally, the distal end 46 may be radiopaque for fluoroscopic visualization of the distal tip region 44 during a catheter procedure.

The guide wire lumen 60 extends through the catheter 34 from a proximal end to a distal end thereof. The C-channel 42 forms a portion (e.g., a channel portion) of the guide wire lumen 60, extending between a channel proximal end 52 and a channel distal end 54. The C-channel 42 serves to contain, but not necessarily constrain, the guide wire 36 therein. In contrast to some catheters that include channels that are substantially "U" shaped, the C-channel 42 is shaped substantially like a letter "C". That is, sides of the C-channel extend inward from a maximum diameter to partially close the channel, as shown more clearly in FIGS. 4 and 5. The "C" shape allows radial removal of the guide wire 36 from the C-channel 42 via a slot 42' (e.g., a channel opening) extending between the walls of the C-channel 42 and opening an interior of the guide wire lumen 60 to an outside of the catheter 34. At the same time, the "C" shape of the C-channel, increases the overall strength of the shaft 38 compared with catheters that have a "U" shaped channel. The increased strength of the shaft allows for greater force to be used in pushing the catheter 34 into the body. The "C" shape of the C-channel also leaks less bodily fluid as compared to catheters that have a "U" shaped channel.

In a preferred embodiment, the C-channel 42 is sufficiently large to allow unhindered radial removal of the guide wire 36 from the C-channel 42 via the slot 42'. Further, the walls of the C-channel 42 and the slot 42' may be formed to be substantially equal in size to or slightly larger than a diameter of a guide wire to be used with the catheter 34, as described in greater detail below. Although it is recognized that the channel proximal end 52 may be located at any location distal of the proximal end 40 of the shaft 38, the channel distal end 54 is preferably located between 10 and 40 cm from the distal end 46 of the catheter shaft 38. The channel distal end 54 may-more preferably be located between 20 and 30 cm and, most preferably, approximately 25 cm from the distal end 46.

Figure 2:
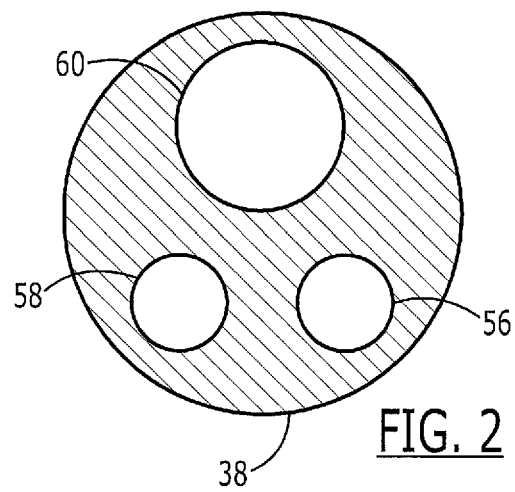
FIG. 2 shows a cross-sectional view of the catheter of FIG. 1 taken along the line 2-2 thereof.
Figure 3:
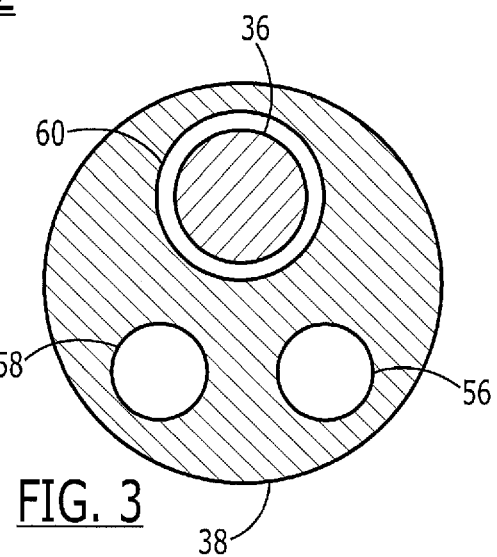
FIG. 3 shows a cross-sectional view of the catheter with the guide wire of FIG. 1 taken along the line 3-3 thereof.
Figure 4:
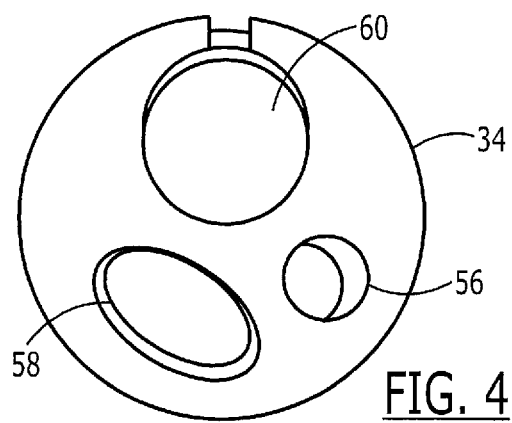
FIG. 4 shows a cross-sectional view of the catheter with the guide wire of FIG. 1 taken along the line 4-4 thereof.
Figure 5:
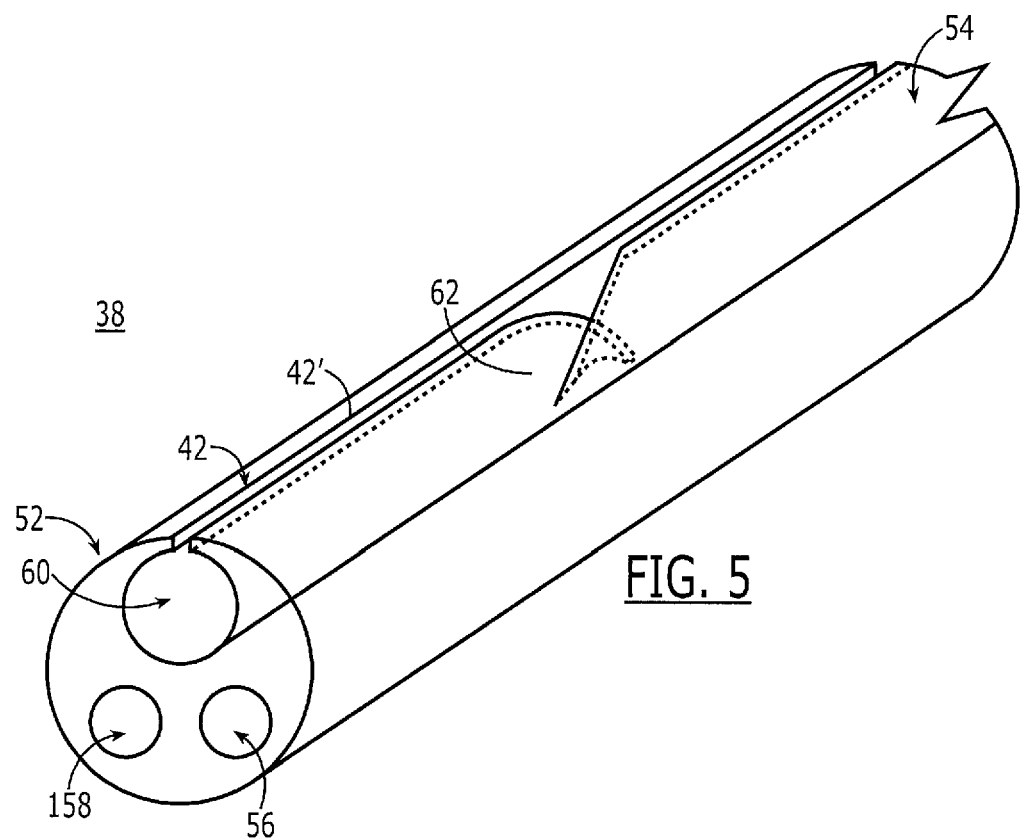
FIG. 5 shows a partially cross-sectional perspective view of the catheter of FIG. 1 showing the formed guide wire ramp thereof taken along the line 4-4 of FIG. 1.

As shown in FIG. 2, proximal to the channel proximal end 52 and a beginning at a sealed proximal portion 52', the guide wire lumen 60 is completely sealed from an outside of the catheter 34. As shown in FIGS. 4 and 5 and described more fully below, the portion of the guide wire lumen 60 between the channel proximal and distal ends 52, 54, respectively, (i.e., the C-channel 42) is open to the outside of the catheter 34 via the slot 42'. The catheter 34 according to this exemplary embodiment also includes ancillary lumens 56 and 58 which may be used for a variety of purposes as would be understood by those of skill in the art. FIG. 3 shows a guide wire 36 received in the distal portion of the guide wire lumen 60. Beginning at a sealed distal portion 54', this portion of the guide wire lumen 60 is also completely sealed from an outside of the catheter 34.

As would be understood by those of skill in the art, the ancillary lumens 56 and 58 may preferably extend longitudinally between the proximal end 40 and the distal end 46 of the shaft 38 so that they may be used, for example, as injection lumens, allowing for high contrast media flow capability for bubble-free opacification and for visualization of a desired anatomical region. Additionally or alternatively, the ancillary lumens 56 and 58 may, for example, be used for or serve as part of another ancillary device, such as a cutting wire or a retrieval balloon, etc.

The guide wire lumen 60 preferably extends longitudinally between the proximal end 40 and the distal end 46 of the shaft 38 in the preferred embodiment and is sized to receive the guide wire 36 slidably therein. As would be understood, the guide wire lumen 60 may be formed integrally with the catheter shaft 38. Alternatively, the guide wire lumen 60 may be a separate tubular member coupled to the catheter shaft 38. In one preferred embodiment, the guide wire lumen 60 is a tubular member which is located proximate the distal end 46 of the shaft 38. It is recognized, though, that the guide wire lumen 60 may be formed anywhere along the shaft 38, and may comprise an extension of the shaft 38 coupled to the distal end 46 thereof. Alternatively, it may run the entire length of the shaft 38.

Figure 6:
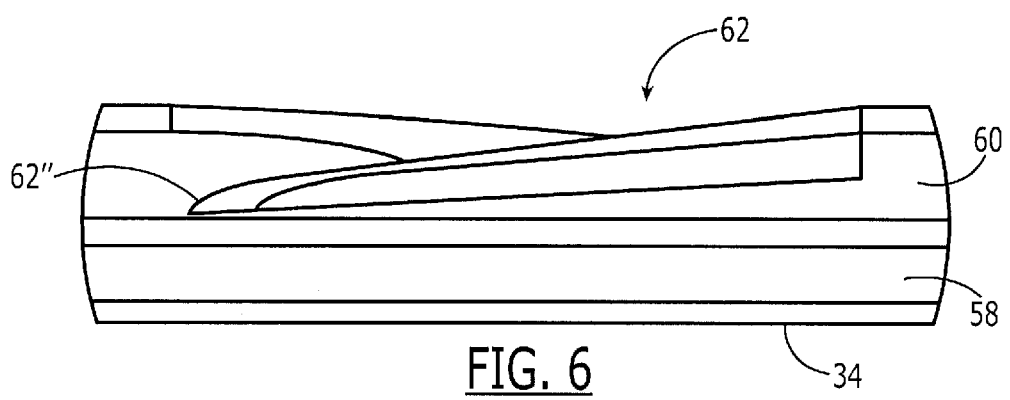
FIG. 6 shows a cross-sectional view of the catheter of FIG. 1 taken along a longitudinal axis thereof.

As shown in FIGS. 5 and 6, a guide wire ramp 62 is formed by a portion of the wall above the guide wire lumen 60. As would be understood by those of skill in the art, the ramp 62 may, for example, be formed by a cut 62' in a portion of the wall of the guide wire lumen 62 extending at an angle from the slot 42' distally for a predetermined length. The substantially triangular portion of the wall which will form the ramp 62 may then be forced into the guide wire lumen 60 and formed as a ramp by, for example, application of a heated mandrel thereto. Those skilled in the art will understand that this same structure may also be created using, for example, a direct molding process, ultrasonic welding or other known techniques. Thus, a pointed end 62" of the ramp 62 will extend into the guide wire lumen 60 with the rest of the surface of the ramp 62 extending upward therefrom to the outer surface of the catheter 34.

In use, when a guide wire 36 has been previously positioned at a desired location within the body, the physician simply inserts the proximal end of the guide wire 36 into the guide wire lumen opening at the distal end of the catheter 34 and slides the catheter 34 distally along the guide wire 36 while gripping the portion of the guide wire 36 extending distally of the distal end of the catheter 34 to retain the guide wire 36 in the desired position. When the proximal end of the guide wire 36 contacts the end 62" of the ramp 62, the proximal end of the guide wire is deflected out of the guide wire lumen 62 through the slot 42'. The physician may then grasp the proximal end of the guide wire 36 and continue to slide the catheter 34 along the guide wire 36 until the desired location is reached. As the guide wire 36 is received within the guide wire lumen 60 only along a short portion of the length of the catheter 34, those skilled in the art will understand that the physician may at all times maintain his grasp on an exposed portion of the guide wire 36 to maintain it in position without the need for guide wire extenders.

If, thereafter, the catheter 34 is to be exchanged for another, the physician simply draws the catheter 34 proximally along the guide wire 36 while grasping the proximal end of the guide wire 36. When the distal end of the catheter 34 exits the body, the physician may grasp the portion of the guide wire 36 extending distally of the catheter 34 and remove the catheter 34 completely from the guide wire 36. The loading process described above may then be repeated for the new catheter 34 to be used. If, however, the physician wishes to exchange the guide wire 36 while maintaining the catheter 34 in a desired position within the body, the following steps are performed. First, while grasping the proximal end of the catheter 34, the physician draws the guide wire 36 proximally out of the guide wire lumen 60 and removes it from the body. Then, the new guide wire 36 is inserted into the channel proximal end 52 and is fed through the guide wire lumen 60 through the C-channel 42 so that it deflects the ramp 62 radially outward to allow the guide wire 36 to pass thereunder, past the channel distal end 54 and out of the distal end of the catheter 34.

If a guide wire 36 has been inserted into the catheter 34 from the proximal end 40, through the C-channel 42 to the distal end 46 and this catheter 34 later needs to be exchanged while maintaining the guide wire 36 in position, the physician grasps the proximal end of the guide wire 36 to maintain it in position and slides the catheter 34 proximally along the guide wire 36 until the channel proximal end 52 is located outside the body. The physician may then grasp the guide wire 36 via the channel proximal end 52 or the slot 42' and draw the proximal end of the guide wire 36 distally through the proximal portion of the guide wire lumen 60 while holding the distal portion of the guide wire 36 stationary to maintain the position of the distal end of the guide wire 36. When the proximal end of the guide wire 36 has been removed from the guide wire lumen 60, the catheter 34 may be drawn proximally from the body with the guide wire 36 sliding out of the C-channel 42 via the slot 42'. When the distal end of the catheter 34 is outside the body, the physician grasps the portion of the guide wire 36 extending distally of the distal end of the catheter 34 and withdraws the catheter 34 from the guide wire 36.

Furthermore, as described above in regard to the exemplary embodiment, the strength of the catheter 34 is improved by cutting into only one side of the slot 42' to form the guide wire ramp 62. The guide wire lumen 60 and the C-channel 42 allow rapid exchange of the catheter assembly 30 when an alternative catheter is necessary during a medical procedure and make it possible to use a shorter guide wire 36 when the guide wire 36 exits the catheter 34 at the channel distal end 54 rather than the proximal end 40.

The present invention may be used, for example, in the treatment of pathologies within a patient's biliary tree. Generally, for the treatment of pathologies within the patient's biliary tree an endoscopic biliary procedure is performed. Methods and devices for using biliary catheters to perform such catheter procedures are disclosed in Weaver et al., U.S. Pat. No. 5,397,302 and Karpiel, U.S. Pat. No. 5,320,602, the disclosures of which are expressly incorporated by reference herein. In an endoscopic biliary procedure, the endoscope is introduced into the mouth of a patient and guided down the patient's alimentary canal through the esophagus, the stomach, and past the pyloric sphincter of the stomach into the duodenum.

Prior to positioning the guide wire 36 within the patient, the catheter assembly 30 is fed into an endoscope and advanced to the opening of the bile duct under visual observation via the endoscope. The catheter 30 is then advanced through the sphincter to enter the bile duct. At this point, a distal end of the guide wire 36 is inserted into the guide wire lumen 60 via the channel proximal end 52 and passed therethrough to the catheter distal end 46. As the guide wire 36 passes through the C-channel 42, it encounters the ramp 62 and deflects the distal end 62" of the ramp 62 radially outward while passing through the lumen 60 to the distal end 46 of the catheter 34. The distal end of the guide wire 36 is then located within the bile duct where it may be guided to the target location using known techniques. As would be understood by those of skill in the art, if desired, the distal end of the guide wire 36 may alternatively be fed into the guide wire lumen 60 through the catheter hub assembly 32 and into the proximal end 40 of the catheter 34 and from there to the distal end 46. However, this reduces the effectiveness of the rapid exchange features of the catheter 34 according to the present invention.

In one method, the guide wire 36 is advanced until its distal tip is positioned within the target area in the biliary tree. For example, the distal tip of the guide wire 36 may be guided through the orifice leading to the papilla of vater for access to the biliary tree. The catheter shaft 38 may then be advanced over the guide wire 36, tracking the catheter assembly 30, until the catheter distal tip region 44 exits the distal end of the endoscope and is positioned within the desired duct. In another method, the guide wire 36 and the catheter assembly 30 are advanced together until the catheter distal end 44 is positioned at the target area. In a third possible method, the catheter assembly 30 is first advanced to near the target area. The guide wire 36 may then be inserted when needed to further advance the catheter 34.

Once the guide wire 36 has been positioned at the target area, catheter procedures may be performed. For example, contrast media, such as radiopaque dye, may be injected through the ancillary lumens 56 or 58 into the common bile duct for visualization of the duct. After the desired catheter procedure has been completed, the catheter assembly 30 may be exchanged or removed from the endoscope, leaving the guide wire 36 in position for other guide wire procedures.

The present invention is described with reference to the embodiment shown in FIGS. 1 to 6. One skilled in the art would understand that changes may be made in details, particularly in matters of shape, size, material and arrangement of parts. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A medical device, comprising:
   a tubular member having a distal end and a proximal end;
   wherein a first opening is defined in the tubular member at a position that is proximal of the distal end;
   wherein a second opening is defined in the tubular member at a position proximal of the first opening;
   a channel extending between the first opening and the second opening, the channel being positioned between a first wall surface of the tubular member and a second wall surface of the tubular member;
   a deflectable ramp defined by the first wall surface and a ramp wall surface formed by a cut region in the tubular member that extends proximally from the second wall surface.

2. The medical device of claim 1, wherein the deflectable ramp is designed to shift between a first configuration where a tip region of the deflectable ramp is deflected radially inward relative to an outer surface of the tubular member and a second configuration where the tip region of the deflectable ramp is disposed adjacent to the outer surface of the tubular member.

3. The medical device of claim 2, wherein the tip member contacts an inner surface of the tubular member when the deflectable ramp is in the first configuration.

4. The medical device of claim 1, wherein the tubular member includes a lumen.

5. The medical device of claim 4, wherein the lumen has a diameter, wherein the channel has a channel width, and wherein the channel width is smaller than the diameter of the lumen.

6. The medical device of claim 1, wherein the tubular member includes one or more visual markers.

7. The medical device of claim 1, wherein the tubular member includes one or more radiopaque markers.

8. The medical device of claim 1, wherein along at least a portion of the channel, the tubular member has a transverse cross-sectional shape that is C-shaped.

9. A catheter, comprising:
   an elongate shaft having a guidewire lumen extending therein, the elongate shaft having an outer surface;
   a channel formed along the outer surface, the channel being disposed between a first axially-extending wall surface of the elongate shaft and a second axially-extending wall surface of the elongate shaft; and
   a deflectable ramp member defined by the first axially-extending wall surface and a ramp wall surface formed by a proximally-extending angled cut in a wall surface of the elongate shaft, the deflectable ramp member being designed to deflect between a first position in which the deflectable ramp member extends into the guidewire lumen and a second position wherein the deflectable ramp member deflects radially outward toward the outer surface of the elongate shaft.

10. The catheter of claim 9, wherein the elongate shaft includes one or more additional lumens.

11. The catheter of claim 9, wherein the guidewire lumen has a diameter, wherein the channel has a channel width, and wherein the channel width is smaller than the diameter of the guidewire lumen.

12. The catheter of claim 9, wherein the elongate shaft includes one or more visual markers.

13. The catheter of claim 9 wherein the elongate shaft includes one or more radiopaque markers.

14. The catheter of claim 9, wherein along at least a portion of the channel, the elongate shaft has a transverse cross-sectional shape that is C-shaped.

15. The catheter of claim 9, wherein a tip of the deflectable ramp member contacts an inner surface of the elongate shaft when the deflectable ramp member is in the first position.

16. A catheter, comprising:
   a tubular member having a lumen extending therein, the tubular member having a tube wall;
   a channel formed in the tube wall between a first axially-extending wall region and a second axially-extending wall region; and
   a deflectable ramp member formed in the tube wall and defined by the first axially-extending wall region and a ramp wall surface formed by a proximally-extending cut in the tube wall, the deflectable ramp member being designed to shift between a first position in which the deflectable ramp member extends into the lumen and a second position wherein the deflectable ramp member is disposed adjacent to the tube wall of the tubular member.

17. The catheter of claim 16, wherein the lumen has a diameter, wherein the channel has a channel width, and wherein the channel width is smaller than the diameter of the lumen.

18. The catheter of claim 16, wherein the tubular member includes one or more visual markers.

19. The catheter of claim 16, wherein the tubular member includes one or more radiopaque markers.

20. The catheter of claim 16 wherein along at least a portion of the channel, the tubular member has a transverse cross-sectional shape that is C-shaped.

\* \* \* \* \*